US009045392B2

(12) United States Patent
Unkefer et al.

(10) Patent No.: US 9,045,392 B2
(45) Date of Patent: Jun. 2, 2015

(54) PREPARATION OF 4-AMINO-2,4-DIOXOBUTANOIC ACID

(71) Applicant: Los Alamos National Security, LLC, Los Alamos, NM (US)

(72) Inventors: Pat J. Unkefer, Los Alamos, NM (US); Rodolfo A. Martinez, Santa Fe, NM (US); David R. Glass, Las Vegas, NM (US)

(73) Assignees: Los Alamos National Security, LLC, Los Alamos, NM (US); New Mexico Highlands University, Las Vegas, NM (US)

( * ) Notice: Subject to any disclaimer, the term of this patent is extended or adjusted under 35 U.S.C. 154(b) by 0 days.

(21) Appl. No.: 13/828,905

(22) Filed: Mar. 14, 2013

(65) Prior Publication Data

US 2014/0275624 A1    Sep. 18, 2014

(51) Int. Cl.
C07C 229/00 (2006.01)
C07C 253/30 (2006.01)
C07C 231/06 (2006.01)

(52) U.S. Cl.
CPC ............. C07C 253/30 (2013.01); C07C 231/06 (2013.01)

(58) Field of Classification Search
CPC .... C07C 229/22; C07C 255/07; C07C 255/17
USPC ........................................................ 562/567
See application file for complete search history.

(56) References Cited

U.S. PATENT DOCUMENTS

| 3,899,585 | A | 8/1975 | Misato et al. |
| 4,336,397 | A | 6/1982 | Cragoe, Jr. et al. |
| 5,922,649 | A | 7/1999 | Pehu et al. |
| 6,083,876 | A | 7/2000 | Jokinen et al. |
| 6,288,240 | B1 | 9/2001 | Martinez et al. |
| 6,329,571 | B1 | 12/2001 | Hiei |
| 6,448,202 | B1 | 9/2002 | Miyazawa et al. |
| 6,555,500 | B1 | 4/2003 | Unkefer et al. |
| 6,593,275 | B1 | 7/2003 | Unkefer et al. |
| 6,703,346 | B2 | 3/2004 | Herold et al. |
| 6,767,865 | B2 | 7/2004 | Den Tandt et al. |
| 6,803,345 | B2 | 10/2004 | Herold et al. |
| 6,831,040 | B1 | 12/2004 | Unkefer et al. |
| 6,906,004 | B2 | 6/2005 | Parrish et al. |
| 7,001,869 | B2 | 2/2006 | Johnson |
| 7,094,735 | B2 | 8/2006 | Herold et al. |
| 7,776,790 | B2 | 8/2010 | Herold et al. |
| 8,551,917 | B2 | 10/2013 | Unkefer |
| 8,759,256 | B2 | 6/2014 | Parrish et al. |
| 8,802,595 | B2 | 8/2014 | Unkefer et al. |
| 2003/0032149 | A1 | 2/2003 | Lalonde |
| 2003/0144147 | A1 | 7/2003 | Herold et al. |
| 2003/0148889 | A1 | 8/2003 | Herold et al. |
| 2003/0153461 | A1 | 8/2003 | Parrish et al. |
| 2003/0153462 | A1 | 8/2003 | Herold et al. |
| 2004/0063582 | A1 | 4/2004 | Johnson |
| 2004/0127364 | A1 | 7/2004 | Herold et al. |
| 2004/0132621 | A1 | 7/2004 | Frisch et al. |
| 2004/0209777 | A1 | 10/2004 | Gemma et al. |
| 2005/0137091 | A1 | 6/2005 | Herold et al. |
| 2005/0170967 | A1 | 8/2005 | Parrish et al. |
| 2005/0232868 | A1 | 10/2005 | Rennie et al. |
| 2006/0090219 | A1 | 4/2006 | Kisaka |
| 2006/0205601 | A1 | 9/2006 | Herold et al. |
| 2007/0105719 | A1 | 5/2007 | Unkefer et al. |
| 2010/0184599 | A1 | 7/2010 | Parrish et al. |
| 2012/0090365 | A1 | 4/2012 | Ersek |
| 2014/0038824 | A1 | 2/2014 | Unkefer et al. |

FOREIGN PATENT DOCUMENTS

| EP | 10955565 A1 | 5/2001 |
| EP | 1647181 | 4/2006 |
| JP | H1059808 | 3/1998 |
| JP | 2005512963 | 5/2005 |
| RU | 2277323 | 6/2006 |
| RU | 2333245 | 9/2008 |
| RU | 2333245 C2 | 9/2008 |
| WO | 0154500 | 8/2001 |
| WO | 03026422 | 4/2003 |
| WO | 03026429 | 4/2003 |
| WO | 2004054360 | 7/2004 |
| WO | 2007056409 | 5/2007 |

OTHER PUBLICATIONS

Meister, "Preparation and Enzymatic Reactions of the Keto Analogues of Asparagine and Glutamine," J. Biol. Chem., 1953, vol. 200, pp. 571-589.
Rooney et al., "Inhibitors of Glycolic Acid Oxidase. 4-Substituted 3-Hydroxy-1H-pyrrole-2,5-dione derivatives," J. Med. Chem., 1983, vol. 26, pp. 700-714.
Ta et al., "Utilization of the Amide Groups of Asparagine and 2-Hydroxysuccinamic Acid by Young Pea Leaves," Plant Physiology, 1984, vol. 75, pp. 527-530.
Williams et al., "Inhibitors of Glycolic Acid Oxidase. 4-Substituted 2,4-Dioxobutanoic Acid Derivatives," J. Med. Chem., 1983, vol. 26, pp. 1196-1200.
International Search Report from PCT/US14/21620 dated Jun. 10, 2014 (citing US4336397, Verbic, T. et al. and Tomassini, J. et al.).

(Continued)

Primary Examiner — Brandon Fetterolf
Assistant Examiner — Blaine G Doletski
(74) Attorney, Agent, or Firm — Mark D. Miller; William K. Nelson

(57) ABSTRACT

A process for synthesizing 4-amino-2,4-dioxobutanoic acid involves reacting diethyl oxalate with sodium ethoxide in ethanol to form a reaction mixture, and afterward adding ethyl cyanoacetate to the reaction mixture and allowing a reaction to proceed under conditions suitable to form a first reaction product of the formula diethyl-2-cyano-3-hydroxybutenedioate, and then isolating the diethyl-2-cyano-3-hydroxybutenedioate, and afterward reacting the diethyl-2-cyano-3-hydroxy-butenedioate with aqueous sodium hydroxide under conditions suitable to form 4-amino-2,4-dioxobutanoic acid.

15 Claims, 1 Drawing Sheet

(56) References Cited

OTHER PUBLICATIONS

Verbic, T. et al., An LFER study of the protolytic equilibria of 4-aryl-2,4-dioxobutanoic acids in aqueous solutions. Journal of the Serbian Chemical Society, Jan. 2007, 72(12):1201-1216. (cited in the International Search Report from PCT/US14/21620 dated Jun. 10, 2014).
Tomassini, J. et al., Inhibition of cap (m7GpppXm)-dependent endonuclease of influenza virus by 4-substituted 2,4-dioxobutanoic acid compounds. Antimicrob Agents Chemother, Dec. 1994, 38(12):2827-37. (cited in the International Search Report from PCT/US14/21620 dated Jun. 10, 2014).
Meister, A., Preparation and Enzymatic Reactions of the Keto Analogues of Asparagine and Glutamine. J. Biol. Chem., 1953, 200:571-589.
Weygand, F., et al., Synthese von 1.5-Diaza-cyclooctan-dion-(4.8)-dicarbosaure-(2.6). Chemische Berichte, 1954, 87(4): 482-488.
Stephani, R.A., Meister, A., Structure of the Dimeric alpha-Keto Acid Analogue of Asparagine. The Jounrnal of Biological Chemistry, Dec. 1971, 246(23):7115-7118.
Ta, T.C., Joy, K.W., and Ireland, R.J., Utilization of the Amide Groups of Asparagine and 2-Hydroxysuccinamic Acid by Young Pea Leaves. Plant Physiology, 1984, 75: 527-530.
Tadashi, A. et al., Herbicidal Composition Containing Pyroglutamic Acid or its Salt, English Abstract of Japanese Patent Publication JPH1059808, Mar. 3, 1998. Machine-generated English translation.
Nanjo, T. et al., "Biological functions of proline in morphogenesis and osmotolerance revealed in antisense transgenic *Arapidopsis thanliana*." The Plant Journal, vol. 18, No. 2 (Feb. 1999) pp. 185-193.
Walkey et al., "The inactivation of virus in cultured shoot tips of *Nicotiana rustica* L." J. Gen. Virol., 1969, 5, 237-241.
Tadashi, A. et al., Herbicidal Composition Containing Pyroglutamic Acid or its Salt, English Abstract of Japanese Patent Publication JPH1059808, Mar. 3, 1998, European Patent Organization, http://www.epo.org/searching/free/espacenet.html.
Method of Constructing Plant Showing Improved Growth Under Regulation of Nitrogen, English Abstract of Russian Patent Publication RU2333245, Sep. 10, 2008, European Patent Organization, http://www.epo.org/searching/free/espacenet.html.
Frisch, G. et al., Microemulsion Concentrates, English Abstract of WIPO Patent Publication WO2004054360, Jul. 1, 2004, European Patent Organization, http://www.epo.org/searching/free/espacenet.html.
English Machine Translation of Japanese Patent Application Publication JP10059808 published on Mar. 3, 1998, the English Machine Translation was accessed and downloaded as early as Apr. 1, 2014.
Brochure: Take Off, Verdesian Life Sciences, LLC, 12 Pages, Aug. 2013.
English Abstract of Japanese Patent Publication JP2005512963, May 12, 2005. The English abstract was accessed and downloaded from European Patent Organization, http://www.epo.org/searching/free/espacenet.html on Aug. 20, 2014.
English Abstract of Russian Patent Publication RU2277323 published on May 10, 2006. The English abstract was accessed and downloaded from http://bd.patent.su/2277000-2277999/pat/servl/servlet4b05.html on Oct. 17, 2014.
English Abstract of Russian Patent Publication RU2006104849 published on Jun. 27, 2006. (Issued as RU2333245) The English abstract was accessed and downloaded from European Patent Organization, http://www.epo.org/searching/free/espacenet.html on Oct. 17, 2014.
English Abstract of WIPO Patent Publication WO2007056409 published on May 18, 2007. The English abstract was accessed and downloaded from European Patent Organization, http://www.epo.org/searching/free/espacenet.html on Oct. 17, 2014.
Weygand, "Synthese von 1.5-Diaza~-cyclooctan-dion(4.8)-dicarbonsaure-(2.6)", Feb. 2, 1954, 482-488—with English Abstract.

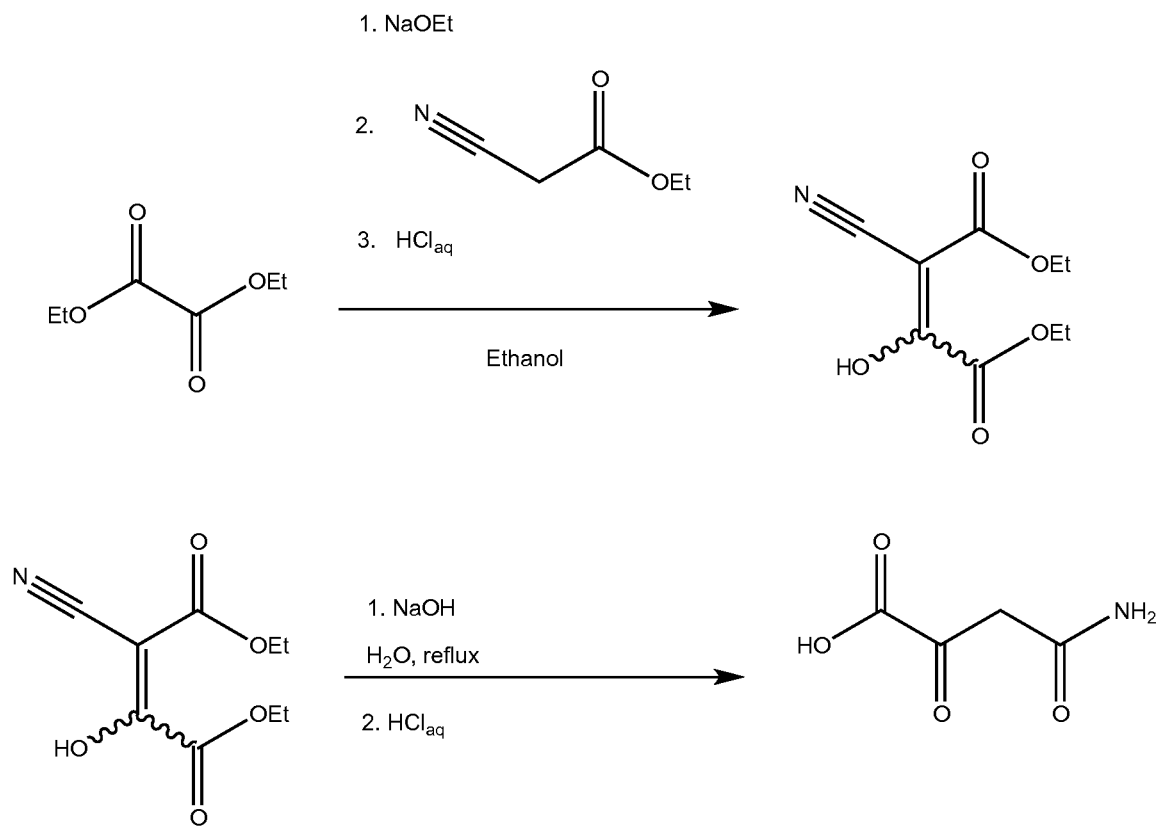

PREPARATION OF 4-AMINO-2,4-DIOXOBUTANOIC ACID

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates to the preparation of 4-amino-2,4-dioxobutanoic acid.

BACKGROUND OF THE INVENTION

The compound 4-amino-2,4-dioxobutanoic acid is a metabolite found in plants (see, for example: Ta et al., "Utilization of the Amide Groups of Asparagine and 2-Hydorxysuccinamic Acid by Young Pea Leaves," Plant Physiology, July 1984, vol. 75, pp. 527-530, incorporated by reference). Meister reported in "Preparation and Enzymatic Reactions of the Keto Analogues of Asparagine and Glutamine," J. Biol. Chem., vol. 200, (1953), pp. 57 1-589, which is incorporated by references, a process for synthesizing 4-amino-2,4-dioxobutanoic acid. This preparation was on a small scale and was expensive because it required crude snake venom.

SUMMARY OF THE INVENTION

The present invention provides a process for synthesizing 4-amino-2,4-dioxobutanoic acid which involves reacting diethyl oxalate with sodium alkoxide in a suitable solvent to form a reaction mixture, and afterward adding ethyl cyanoacetate to the reaction mixture and allowing a reaction to proceed under conditions suitable to form a first reaction product of the formula diethyl-2-cyano-3-hydroxybutenedioate, and isolating said first reaction product, and then reacting said first reaction product with aqueous sodium hydroxide under conditions suitable to form 4-amino-2,4-dioxobutanoic acid.

In an embodiment, a process for synthesizing 4-amino-2,4-dioxobutanoic acid includes the steps of reacting diethyl oxalate with sodium alkoxide in an alcohol solvent to form a reaction mixture, then adding ethyl cyanoacetate to the reaction mixture. After allowing the ingredients to react, the reaction mixture was extracted using dichloromethane and water. The aqueous layer was separated from the dichloromethane layer, acidified, and extracted with additional dichloromethane. The dichloromethane layers were combined. Removal of the dichloromethane left diethyl-2-cyano-3-hydroxybutenedioate. The diethyl-2-cyano-3-hydroxy-butenedioate was combined with aqueous sodium hydroxide to form a reaction mixture that was subjected to conditions suitable for forming 4-amino-2,4-dioxobutanoic acid.

DETAILED DESCRIPTION

This invention is concerned with the synthesis of 4-amino-2,4-dioxobutanoic acid and derivatives thereof. The reaction sequence begins by reacting sodium metal with an alcohol to form a sodium alkoxide. The synthesis was demonstrated using ethanol as the alcohol, which reacted with sodium to form sodium ethoxide. However, it should be understood that other suitable alcohols may also be used (methanol, ethanol, and the like). After forming the sodium ethoxide in ethanol solution, diethyl oxalate was added, and afterward, ethyl cyanoacetate was slowly added. An acidic workup resulted in diethyl-2-cyano-3-hydroxy-butenedioate which was isolated as a pale yellowish solid. Without further purification, the diethyl-2-cyano-3-hydroxy-butenedioate was heated in the presence of aqueous sodium hydroxide. Exemplary chemical reactions are summarized below.

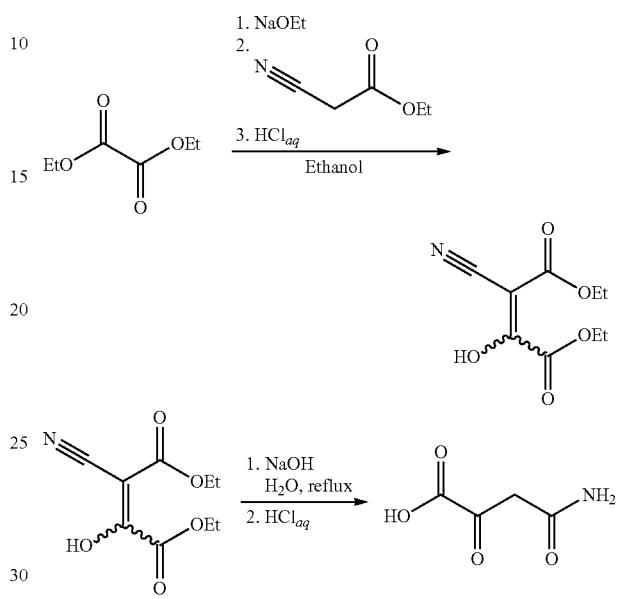

BRIEF DESCRIPTION OF THE DRAWINGS

The drawing depicts exemplary chemical reactions of an embodiment of the present invention.

The details of the synthesis now follow. The synthesis of diethyl-2-cyano-3-hydroxy-butenedioate began by fitting a dry 5-liter Morton flask with a reflux condenser. Absolute ethanol (1040 milliliters) was added to the flask under nitrogen, and sodium metal (35.2 g, 1.53 moles, 1.0 equivalent) was placed into the absolute ethanol also under nitrogen while an ice-water bath was used to cool the flask. After the mixture was stirred for about 6 hours, the ice water bath was removed and the reaction was brought to room temperature. The temperature rose briefly to about 30° C. After about 24 hours, the sodium metal had completely dissolved. Diethyl oxalate (219.2 grams, 1.5 moles, 1.0 equivalent) was added neat in a single portion to the flask. While the reaction mixture was stirring, a solution of ethyl cyanoacetate (169.7 grams, 1.5 moles, 1.0 equivalent) in absolute ethanol (1000 milliliters) was added dropwise at room temperature to the reaction mixture. The addition, which was made at a rate of 1 drop every 2 to 3 seconds, took about 2½ days to complete. Afterward, the reaction mixture was extracted with dichloromethane (1000 milliliters) and deionized water (1000 milliliters). The aqueous layer was extracted with an additional 100 milliliters dichloromethane. The resulting aqueous layer had a pH of about 8-9. The layers were separated. The aqueous layer was acidified to a pH of about 1 with 6 M HCl. The acidic aqueous layer was then extracted with dichloromethane (1000 milliliters) and the layers were separated. The organic layer was evaporated by rotary evaporator to yield diethyl-2-cyano-3-hydroxy-butenedioate as a pale yellowish solid (304 grams, 95%) that was used without any further purification.

The 4-amino-2,4-dioxobutanoic acid was synthesized using the diethyl-2-cyano-3-hydroxy-butenedioate prepared as described above. A 5-liter Morton flask was equipped with an air condenser. Diethyl-2-cyano3-hydroxy-butenedioate (214.2 grams, 1.00 mole, 1.0 equivalent) was dissolved in aqueous sodium hydroxide (1.5 M, 2000 milliliters, 3.0 equivalents) at room temperature in the flask while stirring the contents of the flask. After about one minute, a heating mantle was placed underneath the flask. Using the heating mantle, the flask was heated sufficiently for reflux while the reaction mixture was stirred. After about 4½ hours at reflux, the heat was removed and the reaction mixture was allowed to cool to room temperature and was stirred overnight at room temperature. The reaction solution was placed into an ice-water bath and acidified using 6M HCl until the pH of was equal to about 1. Solids formed after about 5 minutes. The solids were filtered. The colorless solids (27 grams) were analyzed by NMR and were found to include carbonate (13C-NMR $\delta$=162 ppm). The bulk of the water was evaporated using a rotary evaporator at about 40° C. The solids were stirred in acetone (1000 milliliters) and then filtered. The acetone was then removed under a vacuum using a rotary evaporator followed by a vacuum pump to yield the 4-amino-2,4-dioxobutanoic acid in good yield as a viscous yellow oil.

Although the present invention has been described with reference to specific details, it is not intended that such details should be regarded as limitations upon the scope of the invention, except as and to the extent that they are included in the accompanying claims.

What is claimed is:

1. A process for synthesizing 4-amino-2,4-dioxobutanoic acid, comprising:
    reacting diethyl oxalate with sodium alkoxide in a suitable alcohol solvent to form a reaction mixture, and afterward
    adding ethyl cyanoacetate to the reaction mixture and allowing a reaction to proceed under conditions suitable to form a first reaction product of the formula diethyl-2-cyano-3-hydroxy-butenedioate,
    isolating said first reaction product,
    reacting said first reaction product with aqueous sodium hydroxide under conditions suitable to form 4-amino-2, 4-dioxobutanoic acid.

2. A process for synthesizing 4-amino-2,4-dioxobutanoic acid, comprising:
    reacting diethyl oxalate with sodium alkoxide in a first suitable solvent to form a reaction mixture, and afterward
    adding ethyl cyanoacetate to the reaction mixture, and afterward
    extracting the reaction mixture with a suitable organic solvent and water to form an organic layer and an aqueous layer, then
    separating the aqueous layer from the organic layer, then
    acidifying the aqueous layer and extracting the acidified aqueous layer with additional suitable organic solvent to form a second aqueous layer and a second organic layer, then
    combining the first and second organic layers, and
    isolating diethyl-2-cyano-3-hydroxy-butenedioate from the organic layers, then
    reacting the diethyl-2-cyano-3-hydroxy-butenedioate with aqueous sodium hydroxide under conditions suitable to form 4-amino-2,4-dioxobutanoic acid.

3. The process of claim 2, wherein the suitable organic solvent for extracting the reaction mixture is dichloromethane.

4. The process of claim 1 wherein said suitable alcohol solvent is ethanol.

5. The process of claim 2 wherein said first suitable solvent is ethanol.

6. The process of claim 3 wherein said first suitable solvent is ethanol.

7. The process of claim 1 wherein said sodium alkoxide is sodium ethoxide.

8. The process of claim 2 wherein said sodium alkoxide is sodium ethoxide.

9. The process of claim 3 wherein said sodium alkoxide is sodium ethoxide.

10. The process of claim 4 wherein said sodium alkoxide is sodium ethoxide.

11. The process of claim 5 wherein said sodium alkoxide is sodium ethoxide.

12. The process of claim 6 wherein said sodium alkoxide is sodium ethoxide.

13. The process of claim 7 wherein said suitable alcohol solvent is ethanol.

14. The process of claim 8 wherein said first suitable solvent is ethanol.

15. The process of claim 9 wherein said first suitable solvent is ethanol.

* * * * *